United States Patent
Cardinali et al.

(10) Patent No.: US 9,095,418 B2
(45) Date of Patent: Aug. 4, 2015

(54) ANTI-TWIST MECHANISM FOR A MECHANICAL ADVANTAGE TENSIONING DEVICE ON AN ORTHOSIS

(71) Applicant: Breg, Inc., Carlsbad, CA (US)

(72) Inventors: Mathew Cardinali, San Diego, CA (US); Matthew T. Hollister, Encinitas, CA (US)

(73) Assignee: Breg, Inc., Carlsbad, CA (US)

( * ) Notice: Subject to any disclaimer, the term of this patent is extended or adjusted under 35 U.S.C. 154(b) by 322 days.

(21) Appl. No.: 13/831,646

(22) Filed: Mar. 15, 2013

(65) Prior Publication Data
US 2014/0276305 A1 Sep. 18, 2014

(51) Int. Cl.
*A61F 5/00* (2006.01)
*A61F 5/02* (2006.01)

(52) U.S. Cl.
CPC .. *A61F 5/02* (2013.01); *A61F 5/028* (2013.01)

(58) Field of Classification Search
CPC ....... B65B 67/1277; B65B 9/15; B65F 1/062; B65F 1/12; B65F 1/1426; B65F 2230/15; B65F 2240/132; B65F 2210/1675; H01H 43/10; H01H 2043/107; H01H 43/102; H01H 43/106; H01H 11/00; H01H 1/28; B65H 2701/31; B65H 55/00; B65H 18/10; B65H 2301/5121; B65H 2301/5143; B65H 2511/216; B65H 2511/22; B65H 2555/23; B65H 2701/18444; B65H 2701/37; B65H 2701/528; B65H 45/22; B65H 49/16
USPC ............................. 602/19, 32, 36; 2/336–338
See application file for complete search history.

(56) References Cited

U.S. PATENT DOCUMENTS

| | | | |
|---|---|---|---|
| 4,794,916 A | 1/1989 | Porterfield | |
| 5,634,891 A | 6/1997 | Beczak | |
| 5,765,224 A * | 6/1998 | Johnson | 2/44 |
| 5,839,793 A * | 11/1998 | Merrick et al. | 297/484 |
| 5,853,378 A | 12/1998 | Modglin | |
| 5,857,988 A | 1/1999 | Shirley | |
| 5,967,998 A | 10/1999 | Modglin | |
| 6,213,968 B1 | 4/2001 | Heinz | |
| 6,273,029 B1 * | 8/2001 | Gish | 119/792 |
| 6,322,529 B1 | 11/2001 | Chung | |
| 6,342,044 B1 | 1/2002 | Frangi | |
| 6,461,318 B2 | 10/2002 | Freeman | |
| 6,478,759 B1 | 11/2002 | Modglin | |
| 6,517,502 B2 | 2/2003 | Heyman | |
| 6,543,846 B2 * | 4/2003 | Cone | 297/250.1 |
| 6,602,214 B2 | 8/2003 | Heinz | |
| 6,676,620 B2 | 1/2004 | Schwenn | |
| 6,951,547 B1 | 10/2005 | Park | |
| 7,001,348 B2 | 2/2006 | Garth | |
| 7,083,585 B2 | 8/2006 | Latham | |
| 7,118,543 B2 | 10/2006 | Telles | |
| 7,186,229 B2 | 3/2007 | Schwenn | |

(Continued)

FOREIGN PATENT DOCUMENTS

DE 202012100457 U1 3/2012
WO 2012131298 A1 10/2012

*Primary Examiner* — Michael Brown
(74) *Attorney, Agent, or Firm* — Rodney F. Brown

(57) ABSTRACT

An orthosis is provided having a mechanical advantage tensioning device with an anti-twist mechanism. The anti-twist mechanism includes first and second anti-twist members which have a reduced degree of pliability to resist twisting of the orthosis about the mechanical advantage tensioning device.

20 Claims, 6 Drawing Sheets

(56) References Cited

U.S. PATENT DOCUMENTS

| | | |
|---|---|---|
| 7,201,727 B2 | 4/2007 | Schwenn |
| 7,306,571 B2 | 12/2007 | Schwenn |
| 7,473,235 B2 | 1/2009 | Schwenn |
| 7,727,172 B2 | 6/2010 | Wang |
| 7,765,619 B2 | 8/2010 | Jaccard |
| 8,066,654 B2 * | 11/2011 | Sandifer et al. .................. 602/19 |
| 8,142,377 B2 | 3/2012 | Garth |
| 8,172,779 B2 | 5/2012 | Ingimundarson |
| 8,182,438 B2 | 5/2012 | Rumsey |
| 8,303,528 B2 | 11/2012 | Ingimundarson |
| 2007/0073207 A1 | 3/2007 | Sindel |
| 2008/0066272 A1 | 3/2008 | Hammerslag |
| 2008/0249448 A1 | 10/2008 | Stevenson |
| 2010/0168630 A1 | 7/2010 | Cropper |
| 2010/0268141 A1 | 10/2010 | Bannister |
| 2011/0213284 A1 | 9/2011 | Garth |
| 2011/0295169 A1 | 12/2011 | Hendricks |
| 2012/0232450 A1 | 9/2012 | Garth |
| 2012/0245502 A1 | 9/2012 | Garth |
| 2012/0253251 A1 | 10/2012 | Thornton |

\* cited by examiner

ANTI-TWIST MECHANISM FOR A MECHANICAL ADVANTAGE TENSIONING DEVICE ON AN ORTHOSIS

BACKGROUND OF THE INVENTION

The present invention relates generally to an orthosis, and more particularly to an orthosis intended to wrap around a part of the body under tension and support the underlying body part.

An orthosis is commonly constructed to support and stabilize a part of the body on which the orthosis is worn. An orthosis is most frequently worn on a joint such as a knee, ankle, hip, back, elbow, shoulder, wrist, etc. in either a preventative or remedial role. When used preventatively, the orthosis is worn on a healthy joint to reduce the risk of injury when the joint is subjected to undue stress. When used remedially, the orthosis is worn on an injured or infirm joint and reinforces the weakened joint to rehabilitate the joint and/or reduce the risk of further injury or infirmity.

One conventional type of orthosis is termed a lumbar support or lumbar brace which is worn on the lower back and covers the lumbar region. In most cases, lumbar braces are fabricated from pliant materials which allow the wearer a degree of mobility for bending the back. However, pliant materials are also frequently reinforced with strategically placed rigid or semi-rigid members to limit this degree of mobility. A typical lumbar brace has a widened belt configuration with two free ends having a releasable coupling element positioned on each free end. The user dons the lumbar brace by grasping the uncinched brace at each free end, tightly wrapping the lumbar brace around the lumbar region of the body and cinching the brace on the body by releasably connecting the free ends to one another using the releasable coupling elements. The tautness or tension of the cinched lumbar brace laying flat against the lumbar region of the body desirably supports and stabilizes the lower back to reduce the risk of newly injuring the lower back or exacerbating a pre-existing injury or infirmity to the lower back.

It is apparent that the degree of pressure applied by the cinched lumbar brace to the lumbar region of the wearer is a key variable to the effectiveness of the brace in supporting and stabilizing the lumbar region of the back. Accordingly, practitioners in the art have developed numerous means enabling the user to adjust the tension of the lumbar brace while the brace is cinched to the lumbar region of the body, thereby correspondingly enabling the user to adjust the degree of pressure the brace applies to the lumbar region. One such conventional tension adjustment means is termed a lacer system which provides the user with a mechanical advantage for increasing the tension of the cinched lumbar brace. The lumbar brace accommodates the lacer system by providing a discontinuity in the length of the brace between its two free ends which forms a gap therein. The lacer system has two housings mounted on the brace with one being mounted on one side of the gap and the other being mounted on the opposite side of the gap. One or more tensioning laces extend between the two housings across the gap, thereby connecting the brace across the gap. The lacer system enables the user to selectively tension the lumbar brace against the body by manually pulling on the tensioning laces, thereby drawing the two housings and underlying brace on which they are mounted closer together and narrowing the gap. Conversely, the lacer system enables the user to selectively slack or relax the lumbar brace on the body by manually releasing the tensioning laces, thereby displacing the two housings and underlying brace on which they are mounted farther apart and widening the gap.

When the uncinched lumbar brace is stored away from the wearer, the brace is prone to twisting and tangling due to the highly pliant character of the tensioning laces in the lacer system. If the lumbar brace becomes twisted during non-use, it must be untwisted before it can be worn, which can be a cumbersome and tedious task. The present invention recognizes the need for a mechanical advantage tensioning device on an orthosis such as a lumbar brace which substantially prevents or resists twisting. Accordingly, it is generally an object of the present invention to provide an orthosis having a mechanical advantage tensioning device which satisfies the above-recited need. This object and others are accomplished in accordance with the invention described hereafter.

BRIEF SUMMARY OF THE INVENTION

The present invention is characterized as an orthosis comprising a base support worn on the body of a user and a mechanical advantage tensioning device which is cooperative with the base support to selectively provide the orthosis with a tensioned state and a relaxed state. The orthosis applies increased compression to the body of the user when in the tensioned state and applies reduced compression to the body of the user when in the relaxed state.

The base support has a first mounting location and a second mounting location thereon which are spacable a mounting distance apart from one another to define a gap. The mechanical advantage tensioning device includes a first housing, a second housing, a tensioning line, and an anti-twist mechanism. The first housing is mountable on the first mounting location of the base support and the second housing is mountable on the second mounting location of the base support. The mounted first and second housings maintain a substantially coplanar operational position when the orthosis is worn on the body of the user.

The tensioning line has a relatively higher degree of pliability and extends between the first and second housings across the gap, engaging the first and second housings. The orthosis achieves the tensioned state when the tensioning line is pulled in a tensioning direction. The orthosis achieves the relaxed state when the tensioning line is released. The anti-twist mechanism includes a first anti-twist member and a second anti-twist member. Each has a relatively lower degree of pliability than the tensioning line. The first anti-twist member occupies a first coplanar anti-twist position extending between the first and second housings and engaging the first housing and second housing. The second anti-twist member occupies a second coplanar anti-twist position likewise extending between the first and second housings and engaging the first housing and the second housing. The first coplanar anti-twist position and the second coplanar anti-twist position are spaced a distance apart from one another in a same operational plane. The relatively lower degree of pliability of the first and second anti-twist members provides a relatively higher degree of resistance to twisting of the first housing member relative to the second housing member in a twisting direction away from the operational plane than does the tensioning line.

In accordance with an embodiment of the present invention, the base support is relatively flexible and the first and second housings are substantially less flexible. The base support may have a belt-like configuration with a first end and a second end. The first mounting location is more proximal to the first end and the second mounting location is more proximal to the second end.

In accordance with another embodiment of the present invention, the anti-twist mechanism is a continuous closed anti-twist loop. The first anti-twist member is a first segment of the anti-twist loop and the second anti-twist member is a second segment of the anti-twist loop. The anti-twist loop may be a bungee cord. Alternatively or in addition, the anti-twist loop may have a four-sided, rectangle-like configuration. As such, the anti-twist loop has a first set of opposing sides defined by the first and second segments and a second set of opposing sides defined by a third segment representing a first anchoring member and a fourth segment representing a second anchoring member. When the anti-twist loop engages the first and second housing, the first anchoring member engages the first housing along substantially the length of the first anchoring member and the second anchoring member engages the second housing along substantially the length of the second anchoring member. The first and second anti-twist members may be sufficiently elastic to permit some twisting of the first housing member relative to the second housing member away from the coplanar operational position when the orthosis is not being worn on the body of the user and a torque is applied to the first or second anti-twist member. However, the first and second anti-twist members are sufficiently elastic to bias the first and second anti-twist members back toward the coplanar operational position when the orthosis is not being worn on the body of the user and the torque is removed from the first or second anti-twist member.

In accordance with yet another embodiment of the present invention, the first and second anti-twist members are each formed from a length of flexible tubing. Alternatively or in addition, the first and second anti-twist members are each formed from a length of substantially non-stretchable material. In accordance with another embodiment of the present invention, the first anti-twist member slidably engages the first or second housing and the second anti-twist member slidably engages the first or second housing.

The present invention is alternately characterized as an orthosis comprising a base support worn on the body of a user and a mechanical advantage tensioning device which is cooperative with the base support to selectively provide the orthosis with a tensioned state and a relaxed state. The orthosis applies increased compression to the body of the user when in the tensioned state and applies reduced compression to the body of the user when in the relaxed state.

The base support has a first mounting location and a second mounting location thereon which are spacable a mounting distance apart from one another to define a gap. The mechanical advantage tensioning device includes a first housing, a second housing, a tensioning line, and an anti-twist mechanism. The first housing is mountable on the first mounting location of the base support and the second housing is mountable on the second mounting location of the base support. The mounted first and second housings maintain a substantially coplanar operational position when the orthosis is worn on the body of the user.

The tensioning line extends between the first and second housings across the gap, engaging the first and second housings. The orthosis achieves the tensioned state when the tensioning line is pulled in a tensioning direction. The orthosis achieves the relaxed state when the tensioning line is released. The anti-twist mechanism is a continuous closed anti-twist loop having a first segment defining an elastic first anti-twist member and a second segment defining a second anti-twist member. The first and second anti-twist members have a relatively higher degree of elasticity than the tensioning line. The first anti-twist member occupies a first coplanar anti-twist position extending between the first and second housings and engages the first housing and the second housing. The second anti-twist member occupies a second coplanar anti-twist position extending between the first and second housings and engages the first housing and the second housing. The first coplanar anti-twist position and the second coplanar anti-twist position are spaced a distance apart from one another in a same operational plane. The first and second anti-twist members are sufficiently elastic to permit some twisting of the first housing member relative to the second housing member away from the coplanar operational position when the orthosis is not being worn on the body of the user and a torque is applied to the first or second anti-twist member. The first and second anti-twist members are also sufficiently elastic to bias the first and second anti-twist members back toward the coplanar operational position when the orthosis is not being worn on the body of the user and the torque is removed from the first or second anti-twist member.

In accordance with an embodiment of the present characterization of the invention, the anti-twist loop has a four-sided, rectangle-like configuration. As such, the anti-twist loop has a first set of opposing sides defined by the first and second segments and has a second set of opposing sides defined by a third segment representing a first anchoring member and a fourth segment representing a second anchoring member when the anti-twist loop engages the first and second housings. The first anchoring member engages the first housing along substantially the length of the first anchoring member and the second anchoring member engages the second housing along substantially the length of the second anchoring member.

In accordance with this embodiment, the first housing may have a retention slot including a longitudinal slot segment retaining the first anchoring member and the second housing may have a retention slot including a longitudinal slot segment retaining the second anchoring member. The retention slot of the first housing includes a first slot segment substantially orthogonal to the longitudinal slot segment of the first housing and retaining a first portion of the first anti-twist member. The retention slot of the second housing includes a first slot segment substantially orthogonal to the longitudinal slot segment of the second housing and retaining a second portion the first anti-twist member. The retention slot of the first housing also includes a second slot segment substantially orthogonal to the longitudinal slot segment of the first housing and retaining a first portion of the second anti-twist member. The retention slot of the second housing also includes a second slot segment substantially orthogonal to the longitudinal slot segment of the second housing and retaining a second portion of the second anti-twist member.

The present invention is also alternately characterized as an orthosis comprising a base support worn on the body of a user and a mechanical advantage tensioning device which is cooperative with the base support to selectively provide the orthosis with a tensioned state and a relaxed state. The orthosis applies increased compression to the body of the user when in the tensioned state and applies reduced compression to the body of the user when in the relaxed state.

The base support has a first mounting location and a second mounting location thereon which are spacable a mounting distance apart from one another to define a gap. The mechanical advantage tensioning device includes a first housing, a second housing, a tensioning line, and an anti-twist mechanism. The first housing is mountable on the first mounting location of the base support and the second housing is mountable on the second mounting location of the base support. The mounted first and second housings maintain a substantially coplanar operational position when the orthosis is worn on the body of the user.

The tensioning line has a relatively higher degree of pliability and extends between the first and second housings across the gap, engaging the first and second housings. The orthosis achieves the tensioned state when the tensioning line is pulled in a tensioning direction. The orthosis achieves the relaxed state when the tensioning line is released. The anti-twist mechanism includes a first anti-twist member formed from a first length of substantially non-stretchable material and a second anti-twist member formed from a second length of substantially non-stretchable material. Each anti-twist member has a relatively lower degree of pliability than the tensioning line. The first anti-twist member occupies a first coplanar anti-twist position extending between the first and second housings and slidably engages the first housing and the second housing enabling linear displacement of the first anti-twist mechanism independent of the first housing and the second housing. The second anti-twist member occupies a second coplanar anti-twist position extending between the first and second housings and engages the first housing and the second housing enabling linear displacement of the second anti-twist mechanism independent of the first housing and the second housing. The first coplanar anti-twist position and the second coplanar anti-twist position are spaced a distance apart from one another in a same operational plane. The relatively lower degree of pliability of the first and second anti-twist members provides a relatively higher degree of resistance to twisting of the first housing member relative to the second housing member away from the operational plane than does the tensioning line.

In accordance with an embodiment of the present characterization of the invention, the first and second anti-twist members are each formed from a length of flexible tubing. Alternatively, the first and second anti-twist members are each formed from a length of substantially rigid material.

In accordance with another embodiment of the present characterization of the invention, the first housing has a first retention slot retaining a first portion of the first anti-twist member, the second housing has a first retention slot retaining a second portion of the first anti-twist member, the first housing has a second retention slot retaining a first portion of the second anti-twist member, and the second housing has a second retention slot retaining a second portion of the second anti-twist member.

The present invention will be further understood from the drawings and the following detailed description.

DETAILED DESCRIPTION OF THE INVENTION

Figure 1:
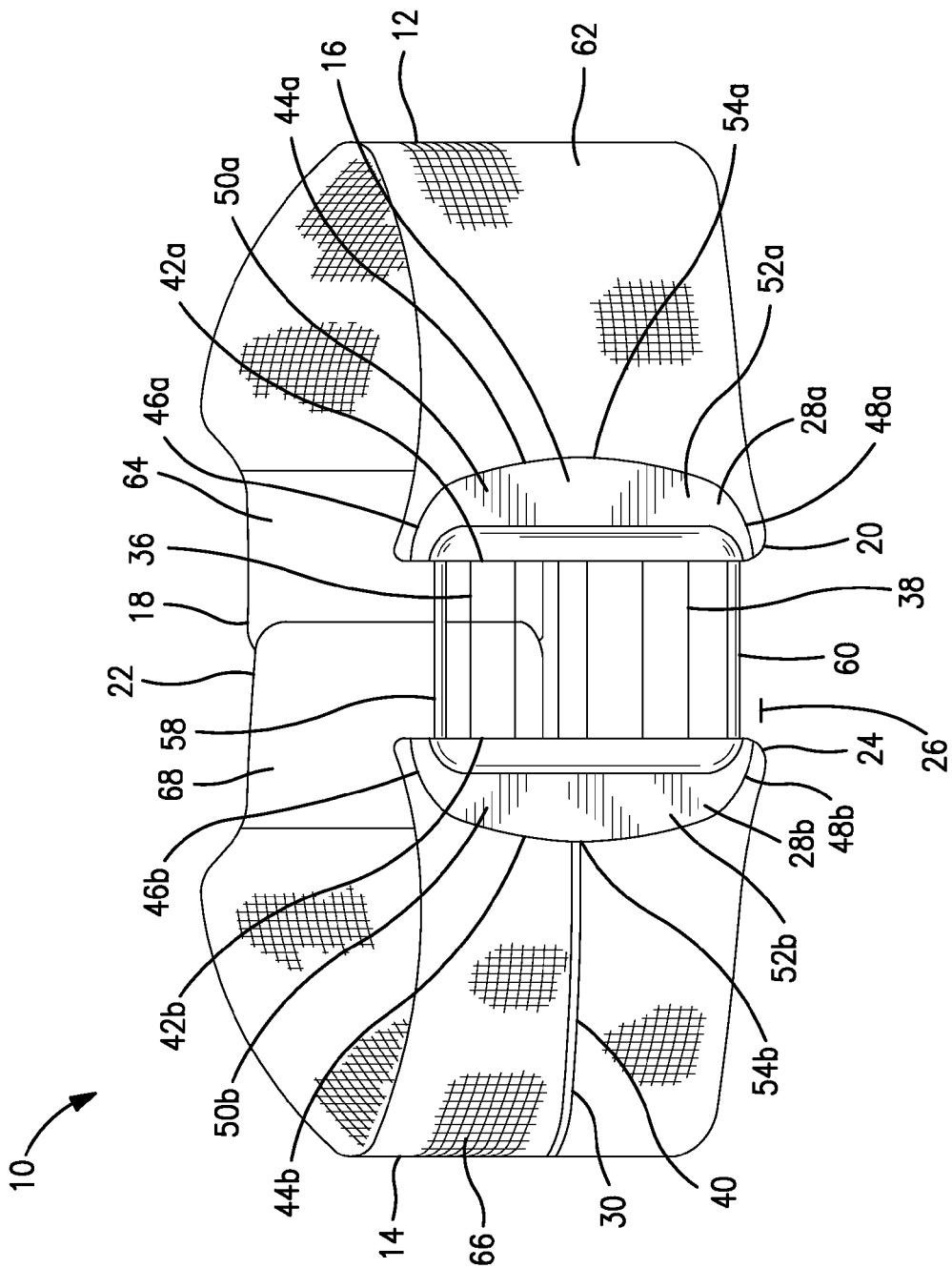
FIG. 1 is a rear perspective view of a lumbar brace including a mechanical advantage tensioning device.
Figure 2:
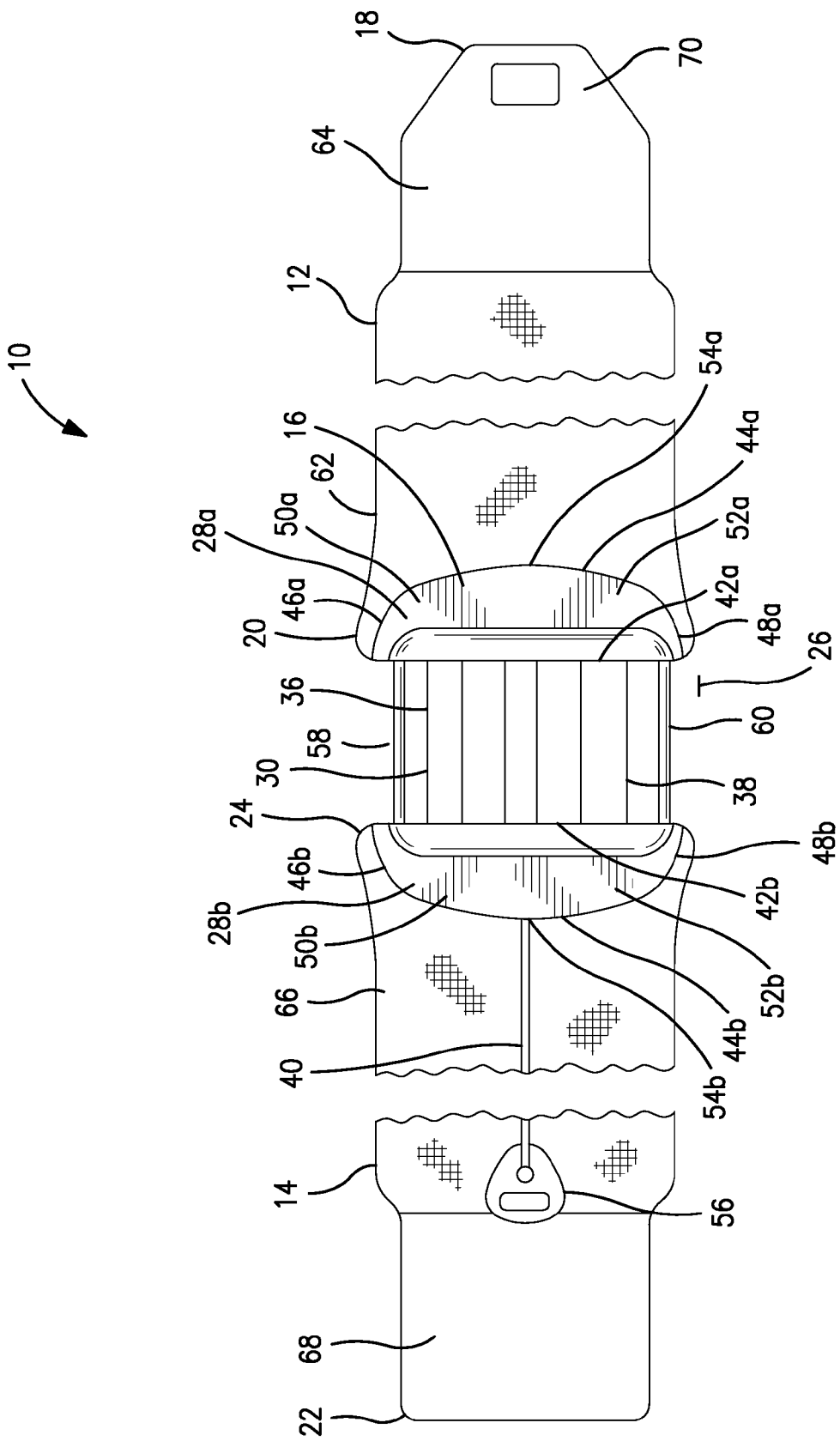
FIG. 2 is a rear plan view of the lumbar brace of FIG. 1 laid out flat to show its outer face.

Referring to FIGS. 1 and 2, a lumbar brace is shown and generally designated 10. The lumbar brace 10 has a belt-like structure resembling a conventional weightlifting belt and is configured to be worn around the lumbar region of a wearer for stabilizing the wearer's lower back. The lumbar brace 10 comprises a first belt segment 12, a separate second belt segment 14 and a mechanical advantage tensioning device 16. The first belt segment 12 has two ends, namely, an attachment end 18 and an adjustment end 20, and the second belt segment 14 similarly has an attachment end 22 and an adjustment end 24. The adjustment ends 20, 24 of the first and second belt segments 12, 14, respectively, are positioned adjacent to one another on the brace 10, but preferably do not engage one another, thereby creating a discontinuity which defines a gap 26 between them.

The mechanical advantage tensioning device 16 includes a first housing 28*a* and a second housing 28*b*. Each of the first and second housings 28*a*, 28*b* has an elongate construction substantially identical to the other to optimize their function and reduce manufacturing costs. Common elements of the first housing 28*a* and the second housing 28*b* are designated in the following description and drawings by the same reference characters with the exception that reference characters for elements of the first housing 28*a* are appended by the suffix "a" and reference characters for elements of the second housing 28*b* are appended by the suffix "b".

The first and second housings 28*a*, 28*b* are positioned on either side of the gap 26, respectively, in the assembled lumbar brace 10. In particular, the first housing 28*a* is mounted on the first belt segment 12 proximal to the adjustment end 20 thereof and the second housing 28*b* is mounted on the second belt segment 14 proximal to the adjustment end 24 thereof. As such, the first and second belt segments 12, 14 function as an effective support base for the first and second housing 28*a*, 28*b*, respectively. Mounting of the housings 28*a*, 28*b* on the belt segments 12, 14, respectively, may be effected by substantially permanent attachment of the housings 28*a*, 28*b* to the belt segments 12, 14 using conventional permanent attachment means such as riveting, gluing, welding, sewing or the like. Alternatively, mounting may be effected by selective releasable attachment using conventional releasable attachment means such as hook and loop fasteners (sold under the trade name VELCRO) or the like.

Figure 4:
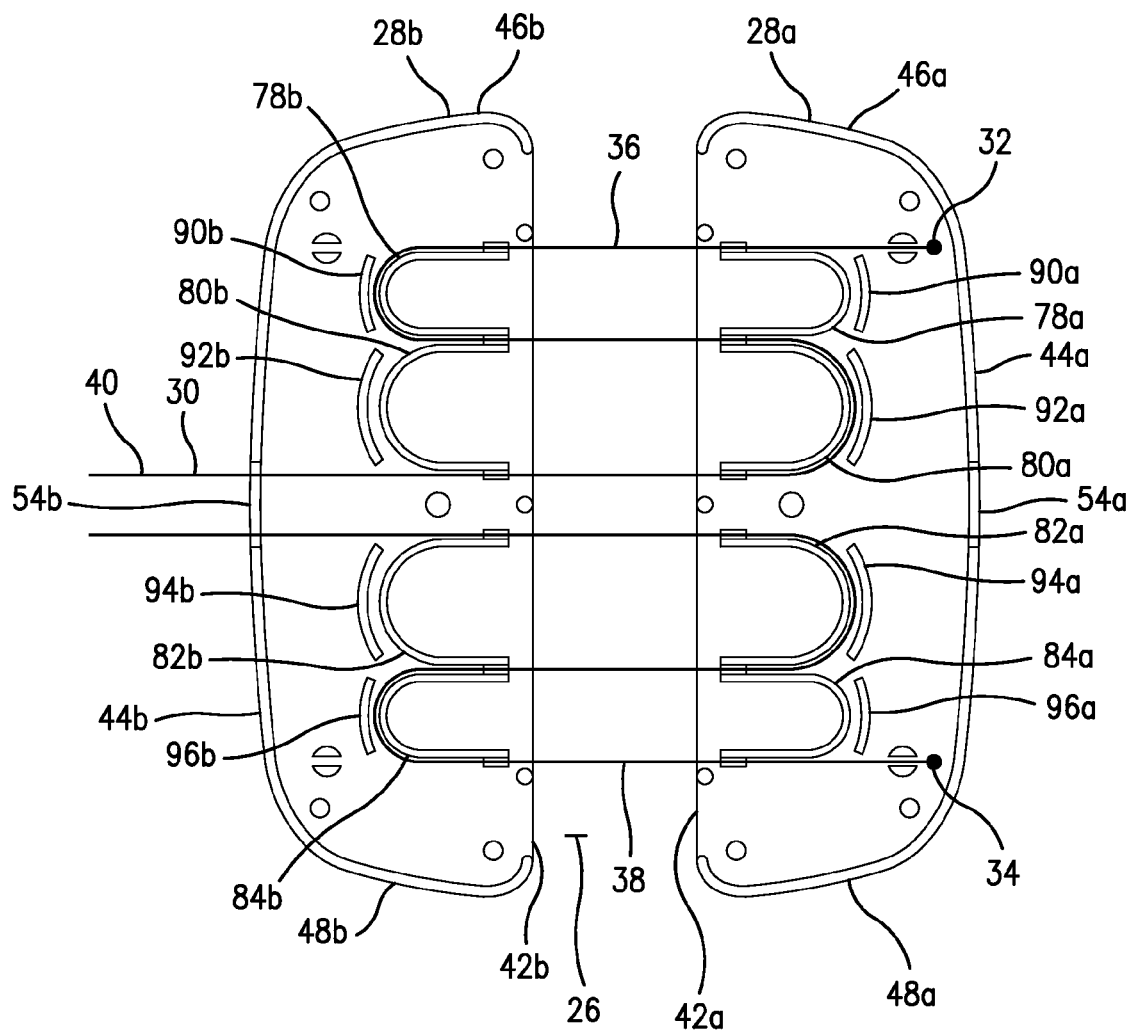
FIG. 4 is a plan view of a pair of the housing bases of FIG. 3 which are operatively positioned opposite one another as when mounted on the lumbar brace and which have a tensioning line threaded through and between them.

The mechanical advantage tensioning device 16 additionally includes a tensioning line 30. The tensioning line 30 is preferably a relatively thin (i.e., small diameter), lightweight, highly-pliant, high-strength, wear-resistant, and friction-resistant monofilament or multi-filament line. In the case of a multi-filament line, the filaments may be woven, braided or twisted together. The tensioning line 30 is also preferably relatively non-stretchable. Lines satisfying the above criteria and having utility herein are commonly characterized as cords, strings, laces, threads, wires or the like. Specific examples include lines which are constructed similar to conventional laces for recreational footwear or conventional drawstrings for window blinds. In any case, the tensioning line 30 has two internal ends, i.e., a first or upper internal end 32 and a second or lower internal end 34 (shown in FIG. 4), both of which are internal to the first housing 28*a*. The tensioning line 30 may be conceptually characterized as a series of continuously connected line segments for purposes of describing the spatial and functional relation between the tensioning line 30 and the housings 28a, 28b. In particular, the tensioning line 30 has a first or upper internal segment 36 proximal to the first internal end 32, a second or lower internal segment 38 proximal to the second internal end 34 and an external segment 40 extending between the first and second internal segments 36, 38, thereby connecting them.

The footprint of each of the first and second housings 28a, 28b approximates a rectangle. Accordingly, each of the first and second housings 28a, 28b has four sides, namely, a medial side 42a, 42b, an opposing lateral side 44a, 44b, an upper side 46a, 46b and an opposing lower side 48a, 48b. Each of the first and second housings 28a, 28b may viewed as being bisected into two essentially identical halves, namely, an upper half or upper portion 50a, 50b and a lower half or lower portion 52a, 52b, for purposes of illustration. In operation, the first internal segment 36 of the tensioning line 30 engages the upper portions 50a, 50b of both the first and second housings 28a, 28b, respectively, and extends from the medial sides 42a, 42b of the upper portions 50a, 50b back and forth between them across the gap 26. Thus, the first internal segment 36 connects the upper portions 50a, 50b of the first and second housings 28a, 28b to one another and correspondingly connects the upper portions of the first and second belt segments 12, 14 to one another proximal to their respective adjustment ends 20, 24.

The second internal segment 38 of the tensioning line 30 similarly engages the lower portions 52a, 52b of the first and second housings 28a, 28b, respectively, and extends from the medial sides 42a, 42b of the lower portions 52a, 52b back and forth between them across the gap 26. Thus, the second internal segment 38 connects the lower portions 52a, 52b of the first and second housings 28a, 28b to one another and correspondingly connects the lower portions of the first and second belt segments 12, 14 to one another proximal to their respective adjustment ends 20, 24.

The end of the first internal segment 36 of the tensioning line 30 distal to the first internal end 32 exits the lateral side 44b of the second housing 28b through a central lateral line opening 54b positioned proximal to the longitudinal midpoint of the second housing 28b, at which point the first internal segment 36 of the tensioning line 30 transitions to the external segment 40. (An identical central lateral line opening 54a is also provided in the lateral side 44a of the first housing 28a although it is not utilized in the present embodiment.) The external segment 40 extends from the central lateral line opening 54b in the second housing 28b in a lateral direction away from the adjustment end 20 and loops through a finger-pull tensioning handle 56 also included in the mechanical advantage tensioning device 16. The external segment 40 reverses direction at the tensioning handle 56, extends in a medial direction back to the central lateral line opening 54b where the external segment 40 transitions to the second internal external segment 38 and reenters the second housing 28b via the central lateral line opening 54b. The tensioning handle 56 is provided with a hook component of a hook and loop fastener on its inner face which enables the user to releasably fasten the tensioning handle 56 to a loop component on the outer face of the first or second belt segment 12, 14 as described hereafter.

The mechanical advantage tensioning device 16 still further includes a first or upper anti-twist member 58 and a second or lower anti-twist member 60. The first and second anti-twist members 58, 60 are preferably both constructed from a material which is substantially less pliant than the material of the tensioning line 30. In accordance with one embodiment shown in FIGS. 1, 2 and 5, the first and second anti-twist members 58, 60 are preferably high-strength and wear-resistant, but are also preferably stretchable and highly elastic relative to the tensioning line 30 or the first and second belt segments 12, 14. On a relative scale, the first and second anti-twist members 58, 60 are preferably more resistant to twisting deformation when subjected to torque than the tensioning member 30 or the first and second belt segments 12, 14, but substantially less resistant than the first and second housings 28a, 28b. A specific example of an anti-twist member satisfying the above criteria and having utility herein is commonly termed a bungee cord or shock cord. However, the present invention is not limited to the above examples and generally encompasses other structures satisfying the above criteria including elastomeric bands and the like.

In operation, the first anti-twist member 58 is positioned above the first internal segment 36 of the tensioning line 30. Like the first internal segment 36, the first anti-twist member 58 also engages the upper portions 50a, 50b of the first and second housings 28a, 28b and extends between the medial sides 42a, 42b of the upper portions 50a, 50b, but only in a single pass across the gap 26. The second anti-twist member 60 is conversely positioned below the second internal segment 38 of the tensioning line 30. Like the second internal segment 38, the second anti-twist member 60 also engages the lower portions 52a, 52b of the first and second housings 28a, 28b and extends between the medial sides 42a, 42b of the lower portions 52a, 52b, but only in a single pass across the gap 26. Further details of the mechanical advantage tensioning device 16, and particularly details of the tensioning line path and the first and second anti-twist member paths internal to the first and second housings 28a, 28b, are set forth later in this disclosure with reference to the remaining FIGS.

With continuing reference to FIGS. 1 and 2, the first belt segment 12 and the second belt segment 14 are both fabricated from an at least somewhat pliant material such as cloth, laminate, solid foam, leather, or the like, which is preferably less pliant than the tensioning line 30. In any case, the material of the belt segments 12, 14 is preferably essentially non-stretchable, at least in the circular direction extending around the circumference of the waist of the wearer. In the present embodiment, the first belt segment 12 has a posterior section 62 formed from a first belt material and an anterior section 64 continuous with the posterior section 62 which is formed from a second belt material. The first belt material is preferably a cloth/foam/cloth laminate and the second belt material is preferably a unitary pliant cloth. The cloth of both the first and second belt materials preferably has a nappy surface which can function as a loop component of a selectively releasable hook and loop fastener. As such, a corresponding hook component of a hook and loop fastener can be releasably attached to any point across essentially the entire inner or outer face of the first belt segment 12. In addition, the added foam layer of the first belt material renders the posterior section 62 overall thicker and less pliant (i.e., stiffer) than the anterior section 64 of the first belt segment 12. The posterior section 62 is also preferably configured with a wider footprint than the anterior section 64.

The second belt segment 14 likewise has a posterior section 66 and an anterior section 68 which are constructed in essentially the same manner as the described above with respect to the first belt segment 12. As a result of this configuration, the present embodiment of the lumbar brace 10 advantageously provides more support and less rearward flexibility to the lumbar region of the wearer while providing less support and more forward flexibility to the abdominal region of the wearer. Although not shown, the first and second belt segments 12, 14, and particularly the thicker, less breathable posterior sections 62, 66 thereof, may have a plurality of small openings formed therethrough for ventilation. The thicker posterior sections 62, 66 may also have a plurality of spaced-apart grooves (not shown) formed therein. The grooves are aligned in correspondence with the longitudinal axis of the wearer's body to provide the stiffened posterior sections 62, 66 with an articulate construction which advantageously facilitates conformance of the lumbar brace 10 to the arcuate contours of the wearer's body. It is also within the scope of the present invention to integrate one or more rigid or semi-rigid reinforcing elements (not shown) such as plates, stays or the like formed from plastics, metals, resins, composites or the like into the lumbar brace 10 and more particularly into the first and/or second belt segments 12, 14 in a manner well known to one of ordinary skill in the art. The reinforcing elements can also be externally attached to the lumbar brace 10 as desired. In any case, any optional reinforcing elements added to the lumbar brace 10 preferably enhance the support function thereof.

Each belt segment 12, 14 has a substantially similar configuration to the other which resembles a half-length of a widened belt that has been bisected along its posterior centerline. The first and second belt segments 12, 14 are preferably sized such that when their adjustment ends 20, 24 are posteriorly connected by the mechanical advantage tensioning device 16, the first and second belt segments 12, 14 and mechanical advantage tensioning device 16 in combination fully encircle the waist of the wearer. This enables the user to cinch the lumbar brace 10 on the body of the wearer in the following manner. The user grasps the attachment ends 18, 22 of the first and second belt segments 12, 14, respectively, and posteriorly positions the adjustment ends 20, 24 against the lower back of the wearer adjacent to the spine, but spaced apart from one another. The gap 26 between the adjustment ends 20, 24 is bridged by the mechanical advantage tensioning device 16 which connects the adjustment ends 20, 24 to one another, even while the mechanical advantage tensioning device 16 preferably remains in a relaxed state. At this stage of the cinching procedure the longitudinal axis of each housing 28a, 28b of the mechanical advantage tensioning device 16, both of which are mounted on the belt segments 12, 14, respectively, is vertically oriented and the medial sides 42a, 42b of the housings 28a, 28b face one another across the gap 26

The user manually wraps the length of the second belt segment 14 anteriorly around one side of the wearer's waist and pulls the attachment end 22 tight, anteriorly positioning it over the wearer's abdomen. The user likewise manually wraps the length of the first belt segment 12 anteriorly around the other side of the wearer's waist and pulls the attachment end 18 tight, anteriorly positioning it over the wearer's abdomen in overlapping relation to the attachment end 22 of the second belt segment 14. A releasable fastening tab 70 is integral with the overlapping attachment end 18 of the first belt segment 12 which has a hook component of a hook and loop fastener on its inner face (not shown). The user releasably fastens the attachment end 18 of the first belt segment 12 to the loop component on the outer face of the second belt segment 14 described above which the attachment end 18 overlaps, thereby cinching the lumbar brace 10 on the body of the wearer. It is further understood that although a hook and loop fastener is described above as a preferred releasable fastening means for cinching the lumbar brace 10 on the body, other conventional releasable fasteners have utility herein such as buckles, zippers, buttons, laces and the like and all fall within the scope of the present invention.

Once the lumbar brace 10 is cinched on the body of the wearer, the lumbar brace 10 is preferably further adjustably tensioned by means of the mechanical advantage tensioning device 16 before the wearer engages in physical activity. Additional details of the mechanical advantage tensioning device 16 are described below with reference to FIG. 3 and with continuing reference to FIGS. 1 and 2. Since the each of the first and second housings 28a, 28b has a construction substantially identical to the other, details of the construction of the housings 28a, 28b are described below only with reference to the first housing 28a. However, it is understood that this same description applies equally to the second housing 28b.

Figure 3:
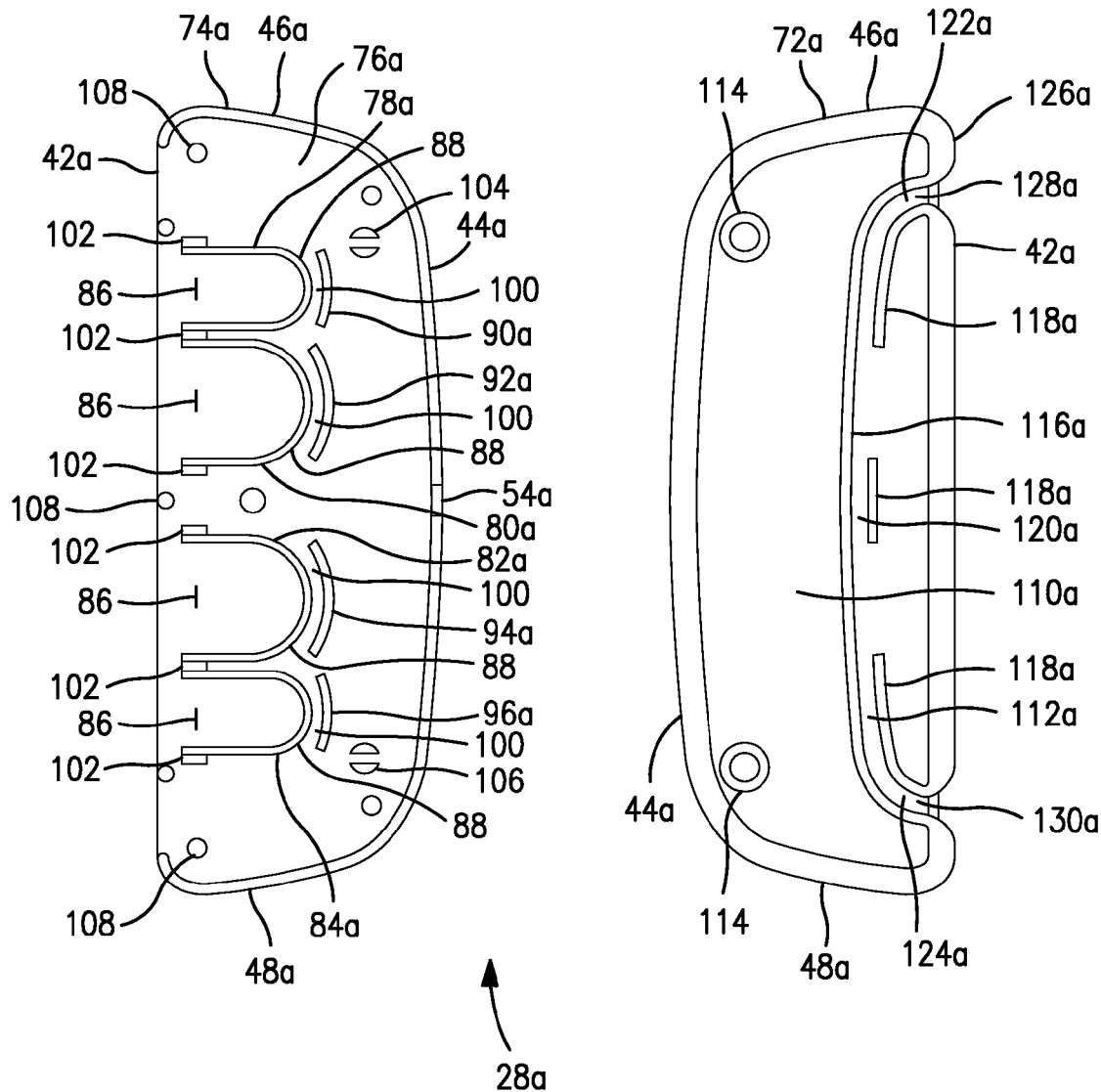
FIG. 3 is a plan view of a housing included in the mechanical advantage tensioning device of FIG. 1 wherein the housing is laid open to show the inner faces of the lid and the base which make up the housing.

The first housing 28a includes an outer plate, termed a lid 72a, and an inner plate, termed a base 74a, which are fastened together. Both are preferably formed from a molded rigid or semi-rigid plastic. Since the lid 72a and the base 74a have identical footprints, their side edges are essentially mirror images of one another so that the lid 72a and base 74a fit flush with one another when fastened together. The lid 72a and base 74a are preferably provided with conventional cooperative press fitting means to facilitate fastening them. In accordance with the present embodiment, the lid 72a and base 74a are entirely separate components when the first housing 28a is unassembled as shown in FIG. 3. However, in accordance with an alternate embodiment not shown, a living hinge can be provided along the opposing medial sides of the lid and base which rotatably joins them together giving the housing a clamshell construction.

The first housing 28a has an elongate configuration when fully assembled with the lid 72a fastened to the base 74a. The upper and lower sides 46a, 48a of the first housing 28a are both fully enclosed. The lateral side 44a of the first housing 28a is nearly fully enclosed with the exception of the central lateral line opening 54a. In contrast, the medial side 42a of the first housing 28a is substantially open to the outside. This configuration desirably enables the tensioning line 30 to follow a path which extends back and forth within the first and second housings 28a, 28b as well as outside of the housings 28a, 28b in a manner described below.

Details of the interior of the base 74a of the first housing 28a are shown in FIG. 3. The base 74a has a planar inner face 76a with four U-shaped wall sections 78a, 80a, 82a, 84a disposed in series across it which rise orthogonally from the inner face 76a. The longitudinal axes of the U-shaped wall sections 78a, 80a, 82a, 84a are also orthogonally oriented relative to the longitudinal axis of the base 74a. Each U-shaped wall section 78a, 80a, 82a, 84a has an open end 86 which faces the medial side 42a of the first housing 28a and an arcuate closed end 88 which faces the lateral side 44a. The inner planar face 76a also has four wall segments 90a, 92a, 94a, 96a disposed in series across it in correspondence with the U-shaped wall sections 78a, 80a, 82a, 84a.

Each wall segment 90a, 92a, 94a, 96a has an arcuate face positioned opposite the arcuate closed end 88 of each U-shaped wall section 78a, 80a, 82a, 84a. The spaces 100 between the arcuate closed ends 88 and the arcuate faces of the wall segments 90a, 92a, 94a, 96a define travel channels for the tensioning line 30 within the interior of the first or second housings 28a, 28b. A plurality of slotted tensioning line guides 102 are also provided on the inner face 76a of the base 74a to maintain the tensioning line 30 in its desired path within the interior of the first housing 28a. A first or upper tensioning anchor 104 and a second or lower tensioning line anchor 106 are also provided on the inner face 76a of the base 74a to secure the first and second internal ends 32, 34, respectively, of the tensioning line 30. In addition, a plurality of support posts 108 are distributed across the inner face 76a of the base 74a to maintain the internal spacing between the lid 72a and base 74a when they are fastened together.

As noted above, the path of the tensioning line 30 generally extends back and forth between the two housings 28a, 28b as well as within the interiors of the two housings 28a, 28b. Details of the full the tensioning line path are described below with reference to FIG. 4. In particular, the first internal end 32 of the tensioning line 30 is secured to the first tensioning line anchor 104 and the first internal segment 36 extends therefrom along the sidewall of the first U-shaped wall section 78a and exits the interior of the first housing 28a through the open medial side 42. The first internal segment 36 extends across the gap 26 between the two housings 28a, 28b and enters the interior of the second housing 28b along the sidewall of the first U-shaped wall section 78b of the second housing 28b. The first internal segment 36 reverses direction when it reaches the closed end 88 of the first U-shaped wall section 78b by curving around it within the travel channel 100. The first internal segment 36 then extends back out of the interior of the second housing 28b by following the opposite sidewall of the first U-shaped wall section 78b. This same back and forth path is repeated within the interior of the first housing 28a, but with the first internal segment 36 following the second U-shaped wall section 80a before returning back to the interior of the second housing 28b.

The second internal segment 38 of the tensioning line 30 follows a path similar to that of the first internal segment 36, but in the lower portions 52a, 52b of the first and second housings 28a, 28b, respectively. In particular, the second internal end 34 of the tensioning line 30 is secured to the second tensioning line anchor 106 and the second internal segment 38 extends therefrom along the sidewall of the forth U-shaped wall section 84a and exits the interior of the first housing 28a through the open medial side 42. The second internal segment 38 extends across the gap 26 between the two housings 28a, 28b and enters the interior of the second housing 28b along the sidewall of the forth U-shaped wall section 84b of the second housing 28b. The second internal segment 38 reverses direction when it reaches the closed end 88 of the fourth U-shaped wall section 84b by curving around it within the travel channel 100. The second internal segment 38 then extends back out of the interior of the second housing 28b by following the opposite sidewall of the fourth U-shaped wall section 84b. This same back and forth path is repeated within the interior of the first housing 28a, but with the second internal segment 38 following the third U-shaped wall section 82a before returning back to the interior of the second housing 28b.

When the first and second internal segments 36, 38 of the tensioning line 30 exit the interior of the second housing 28b via the central lateral line opening 54b in the lateral side 44b of the second housing 28b, the internal segments 36, 38 transition to the external segment 40 of the tensioning line 30 which loops through the tensioning handle 56. The tensioning line 30 is tensioned by pulling the tensioning handle 56 laterally, which draws the external segment 40 of the tensioning line 30 further out of the interior of the second housing 28b. Conversely, the tensioning line 30 is relaxed by releasing the tensioning handle 56 and allowing the external segment 40 to be drawn back into the interior of the second housing 28b. Tensioning the tensioning line 30 draws the opposing first and second housings 28a, 28b closer together, thereby drawing the adjustment ends 20, 24 of the underlying lumbar brace 10 closer together and causing the lumbar brace 10 to fit more snugly around the waist.

Details of the interior of the lid 72a of the first housing 28a are also shown in FIG. 3. The lid 72a has an inner face 110a with a retention slot 112a, alternately termed a retention track, and a plurality of support posts 114 formed thereon. The retention slot 112a is bounded on its sides by a first retention wall 116a and an opposing second retention wall 118a, respectively. The outer face of the lid 72a shown in FIGS. 1 and 2 is preferably raised slightly along the outline of the retention slot 112a to accommodate the underlying retention slot 112a.

Figure 5:
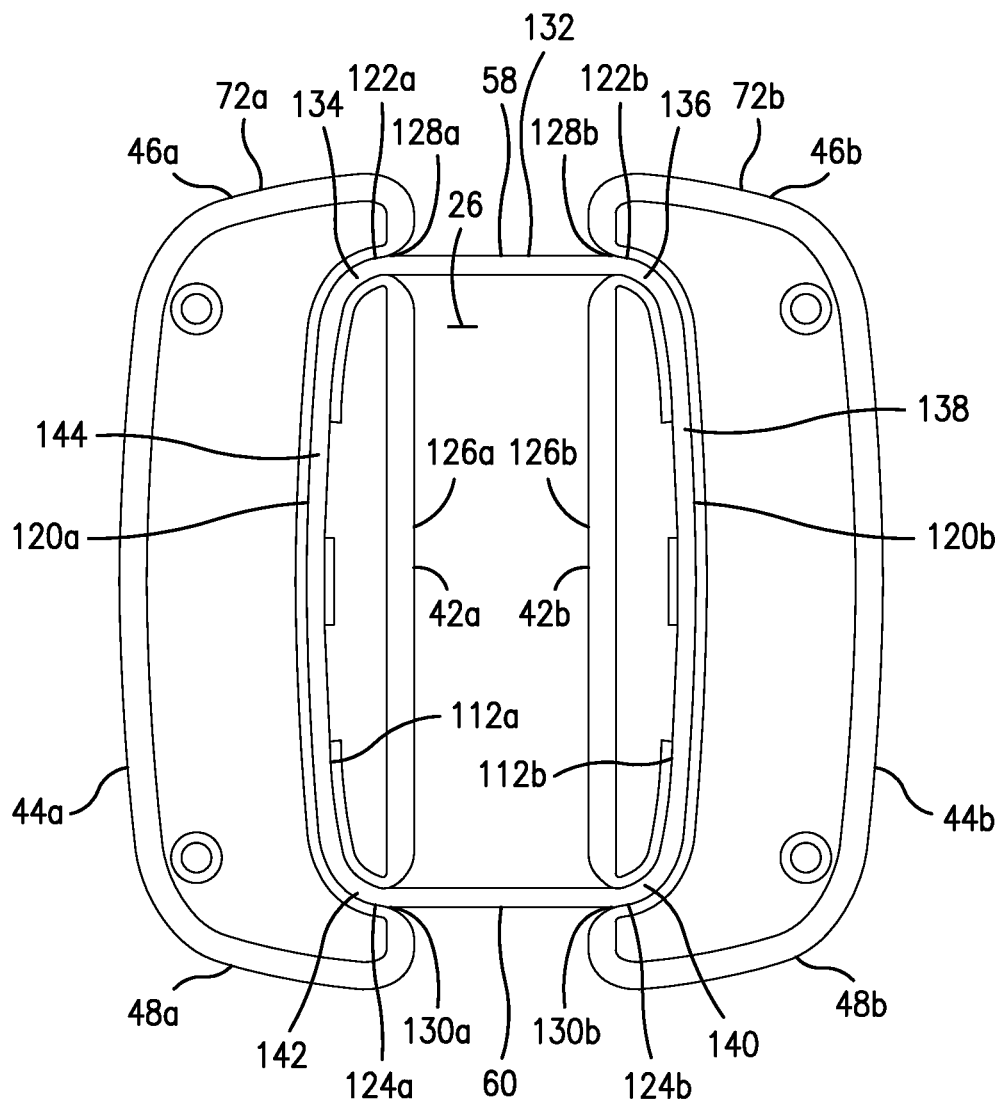
FIG. 5 is a plan view of a pair of the housing lids of FIG. 3 which are operatively positioned opposite one another as when mounted on the lumbar brace and which have an anti-twist mechanism threaded through and between them.

The present embodiment of the retention slot 112a is configured in correspondence of the present embodiment of the first and second anti-twist members 58, 60, wherein the first and second anti-twist members 58, 60 are integrally included in a continuous closed anti-twist loop (shown in FIG. 5). As such, the configuration of the retention slot 112a, in cooperation with the retention slot 112b (likewise alternately termed a retention track) on the inner face 110b of the lid 72b, defines the path of the first and second anti-twist members 58, 60, and more generally the path of the anti-twist loop in its entirety.

The configuration of the retention slot 112a is characterized by a continuous plurality of alternately-oriented slot segments. Specifically, the retention slot 112a has a U-shaped configuration with a longitudinal slot segment 120a, a first or upper slot segment 122a and a second or lower slot segment 124a. The first slot segment 122a medially diverges from the upper end of the longitudinal slot segment 120a via an upper elbow which is an approximately 90° bend. The second slot segment 124a medially diverges from the lower end of the longitudinal slot segment 102a via a similar lower elbow. The lid 72a has a medial edge 126a in which an upper medial slot opening 128a and a lower medial slot opening 130a are formed. The upper medial slot opening 128a is positioned at the end of the first slot segment 122a which is opposite the upper elbow. The diameters of the first slot segment 122a and the upper medial slot opening 128a are comparatively sized to receive the first anti-twist member 58 which snugly fits therein. As such, the upper medial slot opening 128a provides a path for the first anti-twist member 58 between the exterior and the interior of the assembled first housing 28a, and more particularly between the exterior and the first slot segment 122a interior to the first housing 28a.

The lower medial slot opening 130a is similarly positioned at the end of the second slot segment 124a which is opposite the lower elbow. The diameters of the second slot segment 124a and the lower medial slot opening 130a are comparatively sized to receive the second anti-twist member 60 which snugly fits therein. As such, the lower medial slot opening 130a provides a path for the second anti-twist member 60 between the exterior and the interior of the assembled second housing 30a, and more particularly between the exterior and the second slot segment 124a interior to the first housing 28a.

As noted above, the paths of the first and second anti-twist members 58, 60 generally extend back and forth between the two housings 28a, 28b as well as within the interiors thereof. Details of the full paths of the first and second anti-twist members 58, 60 as well as the path of the integral anti-twist loop 132 which encompasses both anti-twist members 58, 60 are described below with reference to FIG. 5. Specifically, the first anti-twist member 58, alternately termed a first anti-twist segment of the anti-twist loop 132, has a first end 134 positioned within the interior of the first housing 28a at the upper elbow in the retention slot 112a which is at the junction of the first and longitudinal slot segments 122b, 120b. The first anti-twist member 58 extends from the upper elbow along a channel defined by the first slot segment 122a, through the upper medial slot opening 128a and out from the interior of the first housing 28a into the gap 26. The first anti-twist member 58 extends across the gap 26, through the upper medial slot opening 128b of the second housing 28b and into the interior thereof along a channel defined by the first slot segment 122b until a second end 136 of the first anti-twist member 58 reaches the upper elbow in the retention slot 112b which is at the junction of the first and longitudinal slot segments 122b, 120b.

The continuous anti-twist loop 132 transitions from the first anti-twist segment 58 to a second anchor segment 138 at the upper elbow and extends orthogonally relative to the first anti-twist segment 58 along a channel defined by the longitudinal slot segment 120b of the retention slot 112b until it reaches the lower elbow in the retention slot 112b which is at the junction of the second and longitudinal slot segments 124b, 120b. It is noted that the diameter of the longitudinal slot segment 120b is comparatively sized to receive the second anchor segment 138 which snugly fits therein. The continuous anti-twist loop 132 transitions from the second anchor segment 138 to a second end 140 of the second anti-twist segment 60 at the lower elbow and extends orthogonally relative to the second anchor segment 138 along a channel defined by the second slot segment 124a, through the lower medial slot opening 130b and out from the interior of the second housing 28b into the gap 26.

The second anti-twist segment 60 extends across the gap 26, through the lower medial slot opening 130a of the first housing 28a and into the interior thereof along a channel defined by the second slot segment 124a until a second end 142 of the second anti-twist member 60 reaches the lower elbow in the retention slot 112a which is at the junction of the second and longitudinal slot segments 124a, 120a. The continuous anti-twist loop 132 transitions from the second anti-twist segment 60 to a first anchor segment 144 at the lower elbow and extends orthogonally relative to the second anti-twist segment 60 along a channel defined by the longitudinal slot segment 120a of the retention slot 112a until it reaches the upper elbow in the retention slot 112a which completes the closed path of the anti-twist loop 132. It is noted that the diameter of the longitudinal slot segment 120a is comparatively sized to receive the first anchor segment 142 which snugly fits therein.

The first and second anti-twist members 58, 60 substantially prevent or resist twisting of the mechanical advantage tensioning device 16 and the overall lumbar brace 10 at the gap 26 by providing a greater counter force to torque applied to the mechanical advantage tensioning device 16 than does the tensioning line 30. If sufficient torque is applied to the lumbar brace 10 to overcome the counter force of the first and second anti-twist members 58, 60 and undesirably twist the lumbar brace 10 at the gap 26, the first and second anti-twist members 58, 60 have sufficient elastic force to restore the lumbar brace 10 to its preferred untwisted condition once the torque withdrawn.

Figure 6:
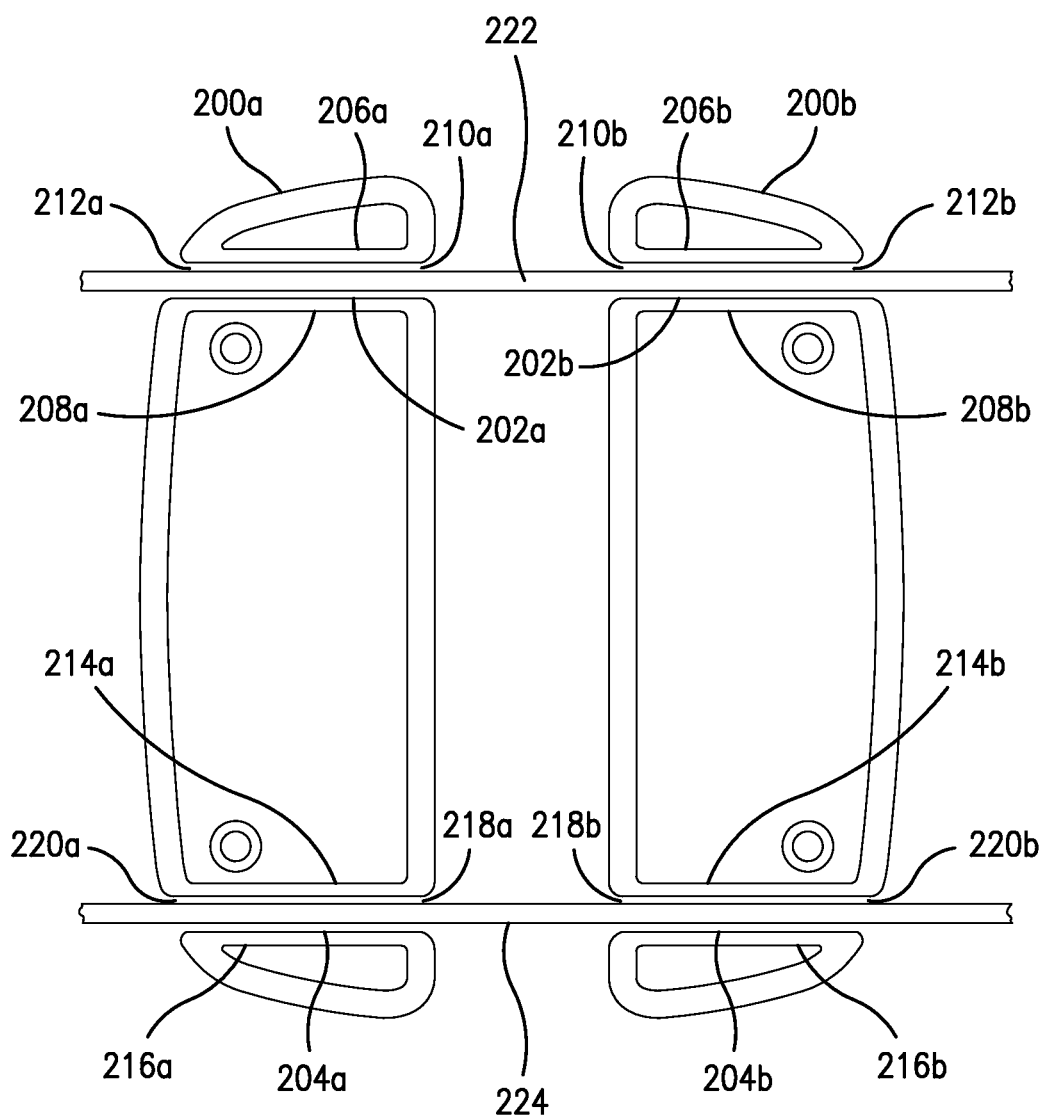
FIG. 6 is a plan view of a pair of housing lids having an alternate construction to accommodate an alternate anti-twist mechanism.

An alternate embodiment of the lids for the first and second housings and correspondingly an alternate embodiment of the first and second anti-twist members are described below with reference to FIG. 6, wherein like reference characters indicate the same or similar elements as the previous embodiment. In accordance with the present embodiment, the alternate lids are lids 200a, 200b, respectively, which may be coupled with the bases 74a, 74b, respectively, to assemble a mechanical advantage tensioning device for an orthosis in substantially the same manner as described above with respect to the previous embodiment. The present lids 200a, 200b differ from the lids 72a, 72b described above primarily in the configuration of the retention slots. Since the each of the lids 200a, 200b has a construction substantially identical to the other, details of the construction of the lids 200a, 200b are described below only with reference to the lid 200a. However, it is understood that this same description applies equally to the lid 200b.

The lid 200a has a first or upper retention slot 202a, alternately termed a first or upper retention track, and a second or lower retention slot 204a, alternately termed a second or lower retention track, which is separate from the first retention slot 202a. The first retention slot 202a is essentially linear and orthogonal to the longitudinal axis of the lid 200a and correspondingly orthogonal to the longitudinal axis of the body of the wearer on which it is worn. The first retention slot 202a is bounded on its sides by a first upper retention wall 206a and an opposing second upper retention wall 208a, respectively. The first retention slot 202a is also open to the housing exterior at both its ends, having an upper medial slot opening 210a at one end of the first retention slot 202a and a upper lateral slot opening 212a at the other end of the first retention slot 202a. The diameters of the first retention slot 202a and the upper medial and lateral slot openings 210a, 212a are comparatively sized to receive the present embodiment of the first anti-twist member described hereafter.

The second retention slot 204a is similarly bounded on its sides by a first lower retention wall 214a and an opposing second lower retention wall 216a, respectively. The second retention slot 204a is also open to the housing exterior at both of its ends, having a lower medial slot opening 218a at one end of the second retention slot 204a and a lower lateral slot opening 220a at the other end of the second retention slot 202a. The diameters of the second retention slot 204a and the lower medial and lateral slot openings 218a, 220a are comparatively sized to receive the present embodiment of the second anti-twist member described hereafter.

The first and second anti-twist members 222, 224 of the present embodiment are preferably separate discontinuous elongate linear structures. The first and second anti-twist members 222, 224 are constructed from one or more materials which are preferably high-strength and wear-resistant. The materials of construction may be substantially the same as those of the first and second anti-twist members 58, 60 described above, but wherein each anti-twist member 222, 224 is configured as an independent linear structure. Alternatively, the materials of construction may be substantially less stretchable than those of the first and second anti-twist members 58, 60 or, in yet another alternative, the materials of construction may even be essentially non-stretchable, at least in the circular direction extending around the circumference of the waist of the wearer. The first and second anti-twist members 222, 224 may also have substantially the same degree of elasticity as the above-described first and second anti-twist members 58, 60, or may be substantially less elastic or, in the alternative, may be substantially inelastic. Exemplary anti-twist members having utility in the present embodiment include rigid or semi-rigid plastic or metal rods, tubes, and the like or pliant plastic tubing and the like. Other exemplary anti-twist members include cable or wire.

One feature of the present embodiment is that the first and second anti-twist members 222, 224 are not anchored to the housings of the mechanical advantage tensioning device. Instead, the first anti-twist member 222 is slidably displacable within the first retention slots 202a, 202b and the upper medial and lateral slot openings 210a, 210b, 212a, 212b, respectively. The second anti-twist member 224 is likewise slidably displacable within the second retention slots 204a, 204b and the lower medial and lateral slot openings 218a, 218b, 220a, 220b, respectively. This enables displacement of the housings of the anti-twist members 222, 224 and permits unencumbered operation of the mechanical advantage tensioning device. Although not shown, it is readily apparent to one of ordinary skill in the art that means can be provided within the scope of the present invention for maintaining the anti-twist members 222, 224 in their respective retention slots and slot openings without anchoring them to the housings or otherwise disrupting the tensioning function of the mechanical advantage tensioning device. In any case, it is apparent that the first and second anti-twist members 222, 224 substantially prevent or resist twisting of the mechanical advantage tensioning device and the overall orthosis to which it is affixed by providing a significant counter force to torque applied to the mechanical advantage tensioning device in a similar manner as the previously described embodiment.

It is apparent to one of ordinary skill in the art that the above-described embodiments of an anti-twist mechanism are readily adaptable to mechanical advantage tensioning devices other than the specific ones shown herein by way of example for purposes of illustration. The present invention is not limited to any one configuration of a mechanical advantage tensioning device and, as such, other mechanical advantage tensioning devices which employ the anti-twist mechanism taught herein fall within the scope of the present invention. Furthermore, the mechanical advantage tensioning device and associated anti-twist mechanism of the present invention are described herein as being mounted on a lumbar brace. However, it is readily apparent to one of ordinary skill in the art from the teaching herein that the mechanical advantage tensioning device of the present invention can readily be adapted for mounting on any number of alternate orthoses, particularly orthoses which are intended to wrap around a part of the body under tension and support the underlying body part.

While the forgoing preferred embodiments of the invention have been described and shown, it is understood that alternatives and modifications, such as those suggested and others, may be made thereto and fall within the scope of the invention.

We claim:

1. An orthosis comprising:
   a base support worn on the body of a user, said base support having a first mounting location thereon and a second mounting location thereon spacable a mounting distance apart from said first mounting location to define a gap; and
   a mechanical advantage tensioning device cooperative with said base support to selectively provide said orthosis with a tensioned state and a relaxed state, wherein said orthosis applies increased compression to the body of the user when in said tensioned state and applies reduced compression to the body of the user when in said relaxed state, and wherein said mechanical advantage tensioning device includes a first housing, a second housing, a tensioning line, and an anti-twist mechanism,
   wherein said first housing is mountable on said first mounting location of said base support and a second housing is mountable on said second mounting location of said base support, and wherein said first and second housings maintain a substantially coplanar operational position when said orthosis is worn on the body of the user,
   wherein said tensioning line has a relatively higher degree of pliability and extends between said first and second housings across said gap and engages said first and second housings, wherein said orthosis achieves said tensioned state when said tensioning line is pulled in a tensioning direction, and wherein said orthosis achieves said relaxed state when said tensioning line is released,
   wherein said anti-twist mechanism includes a first anti-twist member and a second anti-twist member having a relatively lower degree of pliability than said tensioning line, said first anti-twist member occupying a first coplanar anti-twist position extending between said first and second housings and engaging said first housing and said second housing and said second anti-twist member occupying a second coplanar anti-twist position extending between said first and second housings and engaging said first housing and said second housing, wherein said first coplanar anti-twist position and said second coplanar anti-twist position are spaced a distance apart from one another in a same operational plane, and wherein said relatively lower degree of pliability of said first and second anti-twist members provides a relatively higher degree of resistance to twisting of said first housing member relative to said second housing member away from said operational plane than does said tensioning line.

2. The orthosis of claim 1, wherein said base support is relatively flexible and said first and second housings are substantially less flexible.

3. The orthosis of claim 1, wherein said base support has a belt-like configuration with a first end with said first mounting location more proximal thereto and a second end with said second mounting location more proximal thereto.

4. The orthosis of claim 1, wherein said anti-twist mechanism is a continuous closed anti-twist loop and said first anti-twist member is a first segment of said anti-twist loop and said second anti-twist member is a second segment of said anti-twist loop.

5. The orthosis of claim 4, wherein said anti-twist loop is a bungee cord.

6. The orthosis of claim 4, wherein said anti-twist loop has a four-sided, rectangle-like configuration having a first set of opposing sides defined by said first and second segments and having a second set of opposing sides defined by a third segment representing a first anchoring member and a fourth segment representing a second anchoring member when said anti-twist loop engages said first housing and said second housing, wherein said first anchoring member engages said first housing along substantially the length of said first anchoring member and said second anchoring member engages said second housing along substantially the length of said second anchoring member.

7. The orthosis of claim 1, wherein said first and second anti-twist members are sufficiently elastic to permit some twisting of said first housing member relative to said second housing member away from said coplanar operational position when said orthosis is not being worn on the body of the user and a torque is applied to said first or second anti-twist member, and wherein said first and second anti-twist members are sufficiently elastic to bias said first and second anti-twist members back toward said coplanar operational position when said orthosis is not being worn on the body of the user and said torque is removed from said first or second anti-twist member.

8. The orthosis of claim 1, wherein said first and second anti-twist members are each formed from a length of flexible tubing.

9. The orthosis of claim 1, wherein said first and second anti-twist members are each formed from a length of substantially non-stretchable material.

10. The orthosis of claim 1, wherein said first anti-twist member slidably engages said first or second housing and said second anti-twist member slidably engages said first or second housing.

11. An orthosis comprising:
a base support worn on the body of a user, said base support having a first mounting location thereon and a second mounting location thereon spacable a mounting distance apart from said first mounting location to define a gap; and
a mechanical advantage tensioning device cooperative with said base support to selectively provide said orthosis with a tensioned state and a relaxed state, wherein said orthosis applies increased compression to the body of the user when in said tensioned state and applies reduced compression to the body of the user when in said relaxed state, and wherein said mechanical advantage tensioning device includes a first housing, a second housing, a tensioning line, and an anti-twist mechanism,
wherein said first housing is mountable on said first mounting location of said base support and a second housing is mountable on said second mounting location of said base support, and wherein said first and second housings maintain a substantially coplanar operational position when said orthosis is worn on the body of the user,
wherein said tensioning line extends between said first and second housings across said gap and engages said first and second housings, wherein said orthosis achieves said tensioned state when said tensioning line is pulled in a tensioning direction, and wherein said orthosis achieves said relaxed state when said tensioning line is released,
wherein said anti-twist mechanism is a continuous closed anti-twist loop having a first segment defining an elastic first anti-twist member and a second segment defining a second anti-twist member, said first and second anti-twist members having a relatively higher degree of elasticity than said tensioning line, said first anti-twist member occupying a first coplanar anti-twist position extending between said first and second housings and engaging said first housing and said second housing and said second anti-twist member occupying a second coplanar anti-twist position extending between said first and second housings and engaging said first housing and said second housing, wherein said first coplanar anti-twist position and said second coplanar anti-twist position are spaced a distance apart from one another in a same operational plane, and wherein said first and second anti-twist members are sufficiently elastic to permit some twisting of said first housing member relative to said second housing member away from said coplanar operational position when said orthosis is not being worn on the body of the user and a torque is applied to said first or second anti-twist member, and wherein said first and second anti-twist members are sufficiently elastic to bias said first and second anti-twist members back toward said coplanar operational position when said orthosis is not being worn on the body of the user and said torque is removed from said first or second anti-twist member.

12. The orthosis of claim 11, wherein said anti-twist loop is a bungee cord.

13. The orthosis of claim 11, wherein said anti-twist loop has a four-sided, rectangle-like configuration having a first set of opposing sides defined by said first and second segments and having a second set of opposing sides defined by a third segment representing a first anchoring member and a fourth segment representing a second anchoring member when said anti-twist loop engages said first housing and said second housing, wherein said first anchoring member engages said first housing along substantially the length of said first anchoring member and said second anchoring member engages said second housing along substantially the length of said second anchoring member.

14. The orthosis of claim 13, wherein said first housing has a retention slot including a longitudinal slot segment retaining said first anchoring member and said second housing has a retention slot including a longitudinal slot segment retaining said second anchoring member.

15. The orthosis of claim 14, wherein said retention slot of said first housing includes a first slot segment substantially orthogonal to said longitudinal slot segment of said first housing and retaining a first portion of said first anti-twist member and said retention slot of said second housing includes a first slot segment substantially orthogonal to said longitudinal slot segment of said second housing and retaining a second portion said first anti-twist member.

16. The orthosis of claim 15, wherein said retention slot of said first housing includes a second slot segment substantially orthogonal to said longitudinal slot segment of said first housing and retaining a first portion of said second anti-twist member and said retention slot of said second housing includes a second slot segment substantially orthogonal to said longitudinal slot segment of said second housing and retaining a second portion of said second anti-twist member.

17. An orthosis comprising:
a base support worn on the body of a user, said base support having a first mounting location thereon and a second mounting location thereon spacable a mounting distance apart from said first mounting location to define a gap; and
a mechanical advantage tensioning device cooperative with said base support to selectively provide said orthosis with a tensioned state and a relaxed state, wherein said orthosis applies increased compression to the body of the user when in said tensioned state and applies reduced compression to the body of the user when in said relaxed state, and wherein said mechanical advantage tensioning device includes a first housing, a second housing, a tensioning line, and an anti-twist mechanism,
wherein said first housing is mountable on said first mounting location of said base support and a second housing is mountable on said second mounting location of said base support, and wherein said first and second housings maintain a substantially coplanar operational position when said orthosis is worn on the body of the user,
wherein said tensioning line has a relatively higher degree of pliability and extends between said first and second housings across said gap and engages said first and second housings, wherein said orthosis achieves said tensioned state when said tensioning line is pulled in a tensioning direction, and wherein said orthosis achieves said relaxed state when said tensioning line is released,
wherein said anti-twist mechanism includes a first anti-twist member formed from a first length of substantially non-stretchable material and a second anti-twist member formed from a second length of substantially non-stretchable material, each having a relatively lower degree of pliability than said tensioning line, said first anti-twist member occupying a first coplanar anti-twist position extending between said first and second housings and slidably engaging said first housing and said second housing enabling linear displacement of said first anti-twist mechanism independent of said first housing and said second housing and said second anti-twist member occupying a second coplanar anti-twist position extending between said first and second housings and engaging said first housing and said second housing enabling linear displacement of said second anti-twist mechanism independent of said first housing and said second housing, wherein said first coplanar anti-twist position and said second coplanar anti-twist position are spaced a distance apart from one another in a same operational plane, and wherein said relatively lower degree of pliability of said first and second anti-twist members provides a relatively higher degree of resistance to twisting of said first housing member relative to said second housing member away from said operational plane than does said tensioning line.

18. The orthosis of claim 17, wherein said first and second anti-twist members are each formed from a length of flexible tubing.

19. The orthosis of claim 17, wherein said first and second anti-twist members are each formed from a length of substantially rigid material.

20. The orthosis of claim 17, wherein said first housing has a first retention slot retaining a first portion of said first anti-twist member, said second housing has a first retention slot retaining a second portion of said first anti-twist member, said first housing has a second retention slot retaining a first portion of said second anti-twist member, and said second housing has a second retention slot retaining a second portion of said second anti-twist member.

* * * * *